US012740741B2

(12) United States Patent
Liang et al.

(10) Patent No.: US 12,740,741 B2
(45) Date of Patent: Sep. 22, 2026

(54) CONDUCTIVE HYDROGEL PAPER-BASED DEVICE FOR SYNCHRONOUSLY MONITORING PHYSIOLOGICAL AND BIOCHEMICAL PARAMETERS

(71) Applicant: ZHEJIANG UNIVERSITY, Zhejiang (CN)

(72) Inventors: Bo Liang, Zhejiang (CN); Tianyu Li, Zhejiang (CN); Zhichao Ye, Zhejiang (CN); Xuesong Ye, Zhejiang (CN)

(73) Assignee: ZHEJIANG UNIVERSITY, Zhejiang (CN)

( * ) Notice: Subject to any disclaimer, the term of this patent is extended or adjusted under 35 U.S.C. 154(b) by 295 days.

(21) Appl. No.: 18/434,656

(22) Filed: Feb. 6, 2024

(65) Prior Publication Data

US 2024/0237938 A1 Jul. 18, 2024

Related U.S. Application Data

(63) Continuation of application No. PCT/CN2022/090856, filed on May 5, 2022.

(30) Foreign Application Priority Data

Aug. 9, 2021 (CN) ......................... 202110907375.6

(51) Int. Cl.
*A61B 5/00* (2006.01)
*A61B 5/1477* (2006.01)
(Continued)

(52) U.S. Cl.
CPC .......... *A61B 5/4266* (2013.01); *A61B 5/1477* (2013.01); *A61B 5/259* (2021.01); *A61B 5/282* (2021.01)

(58) Field of Classification Search
None
See application file for complete search history.

(56) References Cited

U.S. PATENT DOCUMENTS

2015/0126834 A1* 5/2015 Wang ...................... B32B 38/10
156/247
2020/0060541 A1* 2/2020 Andrade ............ A61B 5/14517
(Continued)

FOREIGN PATENT DOCUMENTS

CN 103558268 2/2014
CN 109060923 12/2018
(Continued)

OTHER PUBLICATIONS

Xu et al. Paper-based wearable electronics iScience 24, 102736, Jul. 23, 2021 (Year: 2021).*
(Continued)

*Primary Examiner* — Jay B Shah
(74) *Attorney, Agent, or Firm* — JCIPRNET

(57) ABSTRACT

A conductive hydrogel paper-based device for synchronously monitoring physiological and biochemical parameters. Self-assembly is implemented on a paper fiber by means of porous PEDOT:PSS hydrogel, such that the paper fiber has good conductivity and good water wettability, thereby achieving efficient electron transport and substance diffusion, and ensuring that the paper fiber can be used as a low-impedance electrocardio sensor and a high-sensitivity electrochemical sensor. Meanwhile, a spontaneous capillary flow effect allows a filter paper to act as a hydrophilic channel of a paper microfluid for capturing and analyzing sweat. During a motion test, a hydrogel paper patch is attached to the surface of skin to acquire electrocardio data and the concentration of a target substance in the sweat, thereby implementing non-invasive monitoring. A flexible, low-cost and multifunctional paper analysis apparatus can
(Continued)

be implemented for synchronously monitoring physiological and biochemical signals in a movement process.

10 Claims, 5 Drawing Sheets

(51) Int. Cl.
*A61B 5/259* (2021.01)
*A61B 5/282* (2021.01)

(56) References Cited

U.S. PATENT DOCUMENTS

| | | | | |
|---|---|---|---|---|
| 2020/0297255 | A1 * | 9/2020 | Martinez .............. | A61B 5/4266 |
| 2020/0333829 | A1 | 10/2020 | Martinez et al. | |

FOREIGN PATENT DOCUMENTS

| | | |
|---|---|---|
| CN | 110658248 | 1/2020 |
| CN | 112932494 | 6/2021 |
| CN | 113647941 | 11/2021 |
| WO | 2013039151 | 3/2013 |
| WO | 2017122178 | 7/2017 |

OTHER PUBLICATIONS

Singh et al. Paper-Based Sensors: Emerging Themes and Applications, Sensors 2018, 18, 2838 (Year: 2018).*

"International Search Report (Form PCT/ISA/210) of PCT/CN2022/090856", mailed on Jul. 15, 2022, with English translation thereof, pp. 1-6.

"Written Opinion of the International Searching Authority (Form PCT/ISA/237) of PCT/ CN2022/090856", mailed on Jul. 15, 2022, pp. 1-4.

Bo Liang et al., "An Integrated Paper-Based Microfluidic Device for Real-Time Sweat Potassium Monitoring", IEEE Sensors Journal, vol. 21, Apr. 2021, pp. 9642-9648.

Qingpeng Cao et al., "Three-dimensional paper-based microfluidic electrochemical integrated devices (3D-PMED) for wearable electrochemical glucose detection", RSC Advances, vol. 9, Feb. 2019, pp. 5674-5681.

Qingpeng Cao et al., "A Smartwatch Integrated with a Paper-based Microfluidic Patch for Sweat Electrolytes Monitoring", Electroanalysis, vol. 33, Nov. 2020, pp. 1-12.

Yunmeng Zhao et al., "A Highly Stretchable and Strain-Insensitive Fiber-Based Wearable Electrochemical Biosensor to Monitor Glucose in the Sweat", Analytical chemistry, Apr. 2019, pp. 1-11.

Xing Xuan et al., "A wearable electrochemical glucose sensor based on simple and low-cost fabrication supported micro-patterned reduced graphene oxide nanocomposite electrode on flexible substrate", Biosensors and Bioelectronics, Feb. 2018, pp. 1-18.

Yongjiu Lei et al., "A MXene-Based Wearable Biosensor System for High-Performance In Vitro Perspiration Analysis", Small, Apr. 2019, pp. 1-11.

Seung Yun Oh et al., "A Skin-Attachable, Stretchable Electrochemical Sweat Sensor for Glucose and pH Detection", ACS applied materials & interfaces, Apr. 2018, pp. 1-42.

Phan Tan Toi et al., "Highly Electrocatalytic, Durable, and Stretchable Nanohybrid Fiber for On-Body Sweat Glucose Detection", ACS applied materials & interfaces, Feb. 2019, pp. 1-35.

Xuecheng He et al., "Integrated Smart Janus Textile Bands for Self-pumping Sweat Sampling and Analysis", ACS sensors, May 2020, pp. 1-21.

Wenya He et al., "Integrated textile sensor patch for real-time and multiplex sweat analysis", Science Advances, Nov. 2019, pp. 1-9.

Xuanbing Cheng et al., "A Mediator-Free Electroenzymatic Sensing Methodology to Mitigate Ionic and Electroactive Interferents' Effects for Reliable Wearable Metabolite and Nutrient Monitoring", Advanced Functional Materials, Dec. 2019, pp. 1-12.

Yuanjing Lin et al., "Porous Enzymatic Membrane for Nanotextured Glucose Sweat Sensors with High Stability toward Reliable Non-invasive Health Monitoring", Advanced Functional Materials, Jun. 2019, pp. 1-8.

Muamer Dervisevic et al., "Transdermal Electrochemical Monitoring of Glucose via High-Density Silicon Microneedle Array Patch", Advanced Functional Materials, Mar. 2021, pp. 1-10.

* cited by examiner

CONDUCTIVE HYDROGEL PAPER-BASED DEVICE FOR SYNCHRONOUSLY MONITORING PHYSIOLOGICAL AND BIOCHEMICAL PARAMETERS

CROSS-REFERENCE TO RELATED APPLICATIONS

This application is a continuation of international PCT application serial no. PCT/CN2022/090856, filed on May 5, 2022, which claims the priority benefit of China application no. 202110907375.6, filed on Aug. 9, 2021. The entirety of each of the above-mentioned patent applications is hereby incorporated by reference herein and made a part of this specification.

TECHNICAL FIELD

The disclosure belongs to the field of integrated monitoring devices, and specifically relates to an integrated conductive hydrogel paper-based device for synchronously monitoring physiological and biochemical parameters.

DESCRIPTION OF RELATED ART

During sports activities, complex changes occur in the body's physiological and biochemical signals. Especially during long-term and long-distance exercise, athletes are prone to dehydration, hypoglycemia, and arrhythmia, which are all risk factors for sports injuries. At present, wearable devices available on the market can detect physiological signals during exercise, but complex but valuable changes in biochemical indicators are ignored most of the time. Changes in these biochemical indicators are important parameters of the body's response during human body exercise. Therefore, this requires synchronously monitoring of physiological and biochemical indicators during sports activities.

Integrated devices that monitor physiological and biochemical activities on the body surface usually consist of sensors with different functions, sweat microfluidic systems, circuit boards, and batteries. In recent years, some studies have been conducted on integrated monitoring devices, and these devices require a high degree of integration during processing. However, different detection modules require different materials and processing technologies, so that a variety of problems may occur, including material mismatch, complex processing procedures, and difficulty in integrating different processes. Therefore, in view of the aforementioned problems, the use of a physiological and biochemical detection device with high integration, flexibility, efficient electronic transmission, non-invasion, and low costs for the integrated process is necessary.

Correct selection of the base material of the device will alleviate the above problems to a large extent. Paper is considered an ideal base material for body-surface sensors and sweat-conducting devices because it is flexible, recyclable, and cheap. Further, as a natural carrier, paper is able to load a large amount of various materials, allowing the preparation of paper-based devices with multiple functions. However, existing research on paper-based devices mainly focuses on modifying conductive materials on paper, such as metal deposition, and printing conductive materials, and does not focus on modifying paper. Under the microscope, the modified material and the base material are independent of each other, and the fusion of the base material and the electrode is not achieved. Further, paper-based devices with fully integrated physiological and biochemical electrodes as well as microfluidics have not yet been reported. Therefore, it is of great significance to develop a new integrated paper-based device for synchronously detecting physiological and biochemical parameters.

SUMMARY

The disclosure aims to design a highly integrated conductive hydrogel paper-based device for synchronously monitoring exercise physiological and biochemical parameters and a test method thereof.

To achieve the above, the technical means adopted by the disclosure are as follows:

A conductive hydrogel paper-based device for synchronously monitoring physiological and biochemical parameters includes a paper-based module and a flexible detection circuit module.

The paper-based module is divided into three parts, a first part is two pieces of electrocardio electrode paper-based patches, a second part is one piece of an electrochemical detection paper-based patch, a third part is one piece of a paper-based microfluidic patch, and the three parts of the patches are integrated and processed on a same paper-based base layer.

Each piece of the electrocardio electrode paper-based patches forms an electrocardio electrode by being added with a conductive hydrogel material through dripping on the paper-based base layer. The electrochemical detection paper-based patch forms a working electrode by being added with a conductive hydrogel material through dripping on the paper-based base, the working electrode is decorated with an electrochemically-sensitive layer, and a reference electrode and a counter electrode are both attached to the paper-based base layer to form a three-electrode system. The conductive hydrogel material is made of a mixture of conductive polymer PEDOT:PSS and ionic liquid. The electrocardio electrodes, the working electrode, the reference electrode, and the counter electrode are individually connected to a conductive printing port of the flexible detection circuit module through electrode connection lines, and respective electrical signals thereof are sent to the flexible detection circuit module for processing and external transmission.

A sweat collection region, a reaction region, and a sweat evaporation region that are not directly connected to one another are arranged on a plane of the paper-based microfluidic patch, and hydrophobic treatment is performed on the rest of the locations. The paper-based microfluidic patch is able to make the reaction region in contact with the three-electrode system on the electrocardio electrode paper-based patches through 3D folding, the sweat evaporation region and the sweat collection region individually contact the reaction region, and sweat collected in the sweat collection region in a folded state is able to penetrate into the reaction region through a capillary action of the paper-based base layer, contact the three-electrode system to generate an oxidation-reduction potential, and then penetrate into the sweat evaporation region to be evaporated.

Preferably, the reference electrode and the counter electrode are printed on the paper-based base layer through a screen printing process.

Preferably, the ionic liquid is dodecylbenzenesulfonic acid or 1-ethyl-3-methylimidazole.

Preferably, the working electrode is further modified with a catalytic material.

Further, the catalytic material is at least one of Pt nanoparticles and Au nanoparticles.

Preferably, the biochemical reagent is one or more of glucose oxidase, glucose dehydrogenase, lactate oxidase, urate oxidase, cholesterol oxidase, phospholipase, amino acid enzyme, horseradish peroxidase, β-hydroxybutyrate dehydrogenase, Prussian blue, and ferrocene methanol.

Preferably, the electrocardio electrodes are two circular paper-based electrodes, and circular edges are provided with connection ports for connection to the electrode connection lines.

Further, each of the connection ports, the electrode connection lines, and the conductive printing port is printed by printing, with a lower layer being an Ag/AgCl layer and an upper layer being a carbon paste layer.

Further, the flexible detection circuit module includes an electrocardio detection module, an electrochemical detection module, and a wireless communication module, the electrocardio detection module is used to receive electrical signals from the two electrocardio electrodes for electrocardio detection, the electrochemical detection module is used to receive an electrical signal from the three-electrode system to perform electrochemical detection on a target substance in sweat, and the wireless communication module is used to send a detection result to an external receiving end.

Further, the external receiving end is a mobile device with a real-time display function.

Compared to the related art, beneficial effects of the disclosure include the following.

(1) Compared to the related art, the manufacturing of the highly integrated device for detecting physiological and biochemical parameters is achieved in the disclosure without the need to design additional sweat flow channels, and no external circuits are required for data transmission and analysis. During detection, the paper-based patch is attached to the skin surface, the sweat flows into the reaction region through the sweat channel and the signal is collected by the electrochemical measurement electrode, and the electrocardio patch synchronously collects electrocardio data in real time. All data are transmitted, analyzed, and displayed on the mobile phone APP through the Bluetooth module of the flexible circuit board, and the collection and presentation of overall physiological and biochemical data are thus achieved.

(2) Conductive polymer gel is used to prepare the paper-based device in the disclosure, and the high-performance paper-based device can be produced without complex processes, without long reaction time, or without complex processing conditions, and paper can be turned into conductive paper.

(3) The electrode base used in the disclosure is paper-based. Using paper as the base takes advantage of the advantages of paper such as water absorption, easy availability, and inexpensiveness, so that the invented electrochemical paper-based patch does not require special hydrophilic treatment, only requires hydrophobic treatment on the non-sensing parts, and has the advantages of simple processing and low costs.

DESCRIPTION OF THE EMBODIMENTS

The disclosure is further elaborated and described together with accompanying drawings and specific embodiments in the following paragraphs. The technical features of various embodiments of the disclosure may be combined accordingly as long as they do not conflict with each other.

Figure 1:
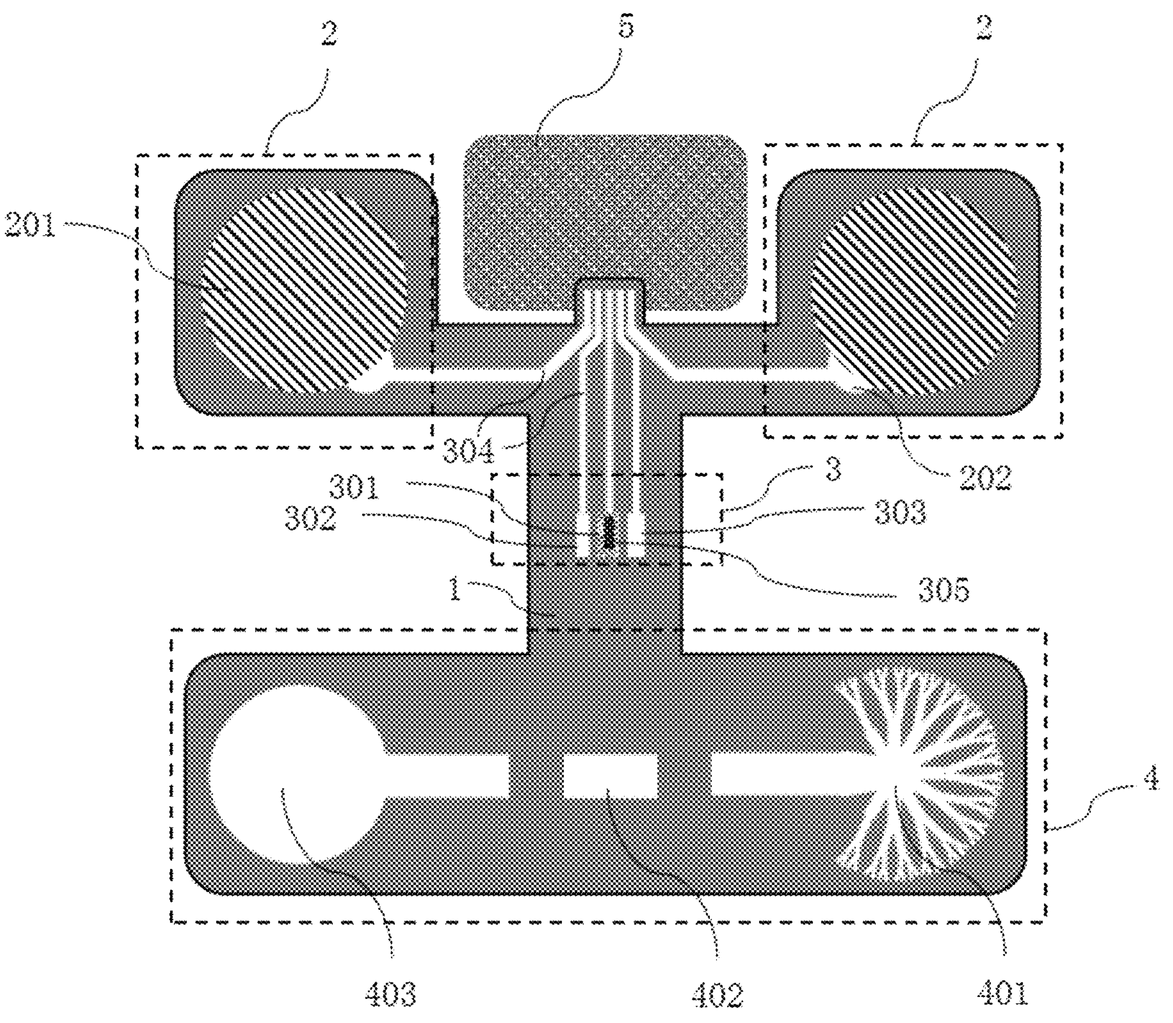
FIG. 1 is a schematic top view of a conductive hydrogel paper-based device for synchronously monitoring physiological and biochemical parameters during exercise according to the disclosure.

As shown in FIG. 1, in a preferred embodiment of the disclosure, a conductive hydrogel paper-based device for synchronously monitoring physiological and biochemical parameters is provided, and a main structure thereof may include two parts including a paper-based module and a flexible detection circuit module 5. The paper-based module is mainly used as a sensor part to obtain an electrical signal related to the physiological and biochemical parameters, while the flexible detection circuit module 5 acts as a signal processing part of the electrical signal. The specific structure and functional implementation forms of the two parts are described in detail in the following paragraphs.

Herein, the paper-based module is divided into three parts on a plane according to functions, a first part is two pieces of electrocardio electrode paper-based patches 2, a second part is one piece of an electrochemical detection paper-based patch 3, a third part is one piece of a paper-based microfluidic patch 4, and the three parts of the patches are integrated and processed on a same paper-based base layer 1. The entire paper-based base layer 1 is in an I-shape, the electrochemical detection paper-based patch 3 is located in the middle, the two pieces of the electrocardio electrode paper-based patches 2 are located at both ends of a top portion of the electrochemical detection paper-based patch 3, and the paper-based microfluidic patch 4 is located at a bottom portion of the electrochemical detection paper-based patch 3.

The two pieces of the electrocardio electrode paper-based patches 2 have a same structure and are symmetrically distributed. Each piece of the electrocardio electrode paper-based patches 2 forms an electrocardio electrode 201 by being added with a conductive hydrogel material through dripping on the paper-based base layer 1. The paper-based base layer 1 itself has its inherent water absorption ability of paper, so the conductive hydrogel material may infiltrate the paper after being dripped, and that an infiltrated region on the paper forms a conductive hydrogel electrode through utilizing its conductive ability. In this embodiment, the electrocardio electrodes 201 are two circular paper-based electrodes, and infiltration regions are circular. Further, in order to facilitate the wiring of the electrocardio electrodes 201, circular edges may be provided with connection ports 202 for connection to electrode connection lines 304. The connection ports 202 may be printed on the paper-based base layer 1 through a screen printing process.

In addition, similarly, a working electrode 301 of the electrochemical detection paper-based patch 3 is also formed by being added with a conductive hydrogel material through dripping on the paper-based base 1, and specific implementation is consistent with that of the electrocardio electrodes 201. A reference electrode 302 and a counter electrode 303 are both attached to the paper-based base layer 1 to form a three-electrode system. The reference electrode 302 and the counter electrode 303 may be printed on the paper-based base layer 1 through a screen printing process.

The abovementioned various electrodes function to form electrical signals related to an object to be detected, and these electrical signals need to be transmitted to the flexible detection circuit module 5 through connection lines. Therefore, a plurality of electrode connection lines 304 need to be printed on the paper-based base layer 1, and the electrocardio electrodes 201, the working electrode 301, the reference electrode 302, and the counter electrode 303 are individually connected to the flexible detection circuit module 5 through the electrode connection lines 304. In order to facilitate the connection of the flexible detection circuit module 5, the conductive printing port may be printed on the paper-based base layer 1. All electrode connection lines 304 are first connected to the conductive printing port, and then the flexible detection circuit module 5 is connected to the conductive printing port, thereby sending respective electrical signals to the flexible detection circuit module 5 for processing and external transmission. In this way, the flexible detection circuit module 5 may be designed to be pluggable for reuse, and only the paper-based module needs to be replaced. The flexible detection circuit module 5 may use a flexible printed circuit board.

In addition, in order to detect a target substance in sweat, the working electrode 301 may be modified with an electrochemically-sensitive layer 305. A specific type of an electrochemically-sensitive material needs to be determined according to the target substance to be detected, and it must be able to undergo an oxidation-reduction reaction with the target substance to generate an oxidation-reduction potential. The electrochemically-sensitive material may react chemically with a target analyte as a reactant to generate a reaction product or may also be used as a catalyst to catalyze the chemical reaction of the target analyte to produce a product. Therefore, in the disclosure, the electrochemically-sensitive layer 305 may be a biochemical reagent or a catalytic material. The biochemical reagent may be selected from one or more of glucose oxidase, glucose dehydrogenase, lactate oxidase, urate oxidase, cholesterol oxidase, phospholipase, amino acid enzyme, horseradish peroxidase, β-hydroxybutyrate dehydrogenase, Prussian blue, and ferrocene methanol. For instance, if the target substance detected is glucose in sweat, glucose oxidase may be modified on the working electrode 301. In addition, the catalytic material may be modified before being modified with the biochemical reagent to improve electrode sensitivity. The catalytic material may be selected from at least one of Pt nanoparticles and Au nanoparticles.

In addition, in this embodiment, the conductive hydrogel material is made of a mixture of conductive polymer PEDOT:PSS and ionic liquid, and both materials need to be fully infiltrated into the paper-based base layer 1. Herein, the ionic liquid is dodecylbenzenesulfonic acid DBSA, 1-ethyl-3-methylimidazole EMIM, or other ionic solutions with relatively high ionic strength. In an actual preparation process, a hydrophobic layer pattern may be printed using a wax spray printer on outer edges of the electrocardio electrodes 201 and the working electrode 301 on the paper-based base layer 1. A sufficient amount of PEDOT:PSS is then dripped into ranges where the electrocardio electrodes 201 and the working electrode 301 are located, and the paper-based base layer 1 in the regions where the electrodes are located is fully infiltrated. A sufficient amount of ionic liquid is then dripped into the ranges where the electrocardio electrodes 201 and the working electrode 301 are located to fully infiltrate the paper-based base layer 1 in the regions where the electrodes are located, and a conductive paper-based hydrogel electrode is thereby formed.

In this device, the conductive hydrogel material is used to infiltrate the paper-based base layer 1 to form the electrocardio electrodes 201 and the working electrode 301, instead of simply using screen printing, and the main purpose is to improve the conductivity and make the electrodes more sensitive and stable. Different from the preparation of flat paper-based screen-printed electrodes, a conductive paper-based hydrogel material used in the disclosure has good conductivity. Further, relying on a 3D spatial structure of a paper fiber in the paper-based base layer 1 and the hydrogel itself, the two may be combined into a 3D gel network with more holes, which is beneficial to electron transmission and the attachment of nanoparticles and enzymes. The hydrogel material has good water wettability and is suitable for testing in a sweat environment, and the hydrogel material also has better mechanical strength and biocompatibility than screen-printed solid electrodes. Since PEDOT:PSS is a conductive polymer, the addition of ionic liquid weakens the electrostatic adsorption force between PEDOT groups and PSS groups. More conductive PEDOT groups are exposed, the π-π group conjugated system has increased, and the delocalization ability of electrons is improved, which is the fundamental reason for the significant improvement in conductivity.

Figure 2:
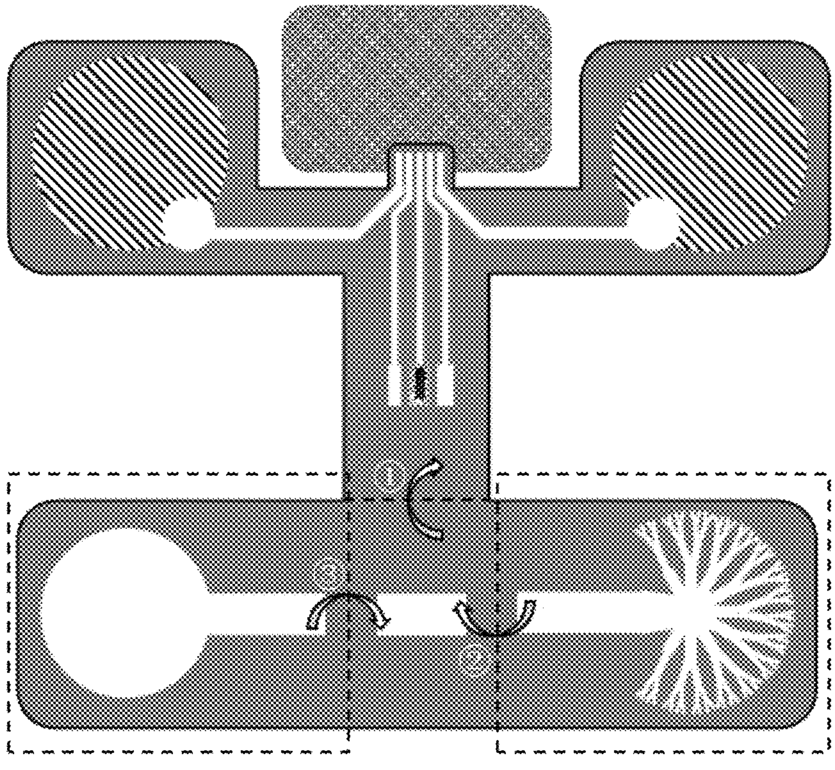
FIG. 2 is a schematic view of a folded plane of a paper-based microfluidic patch.
Figure 3:
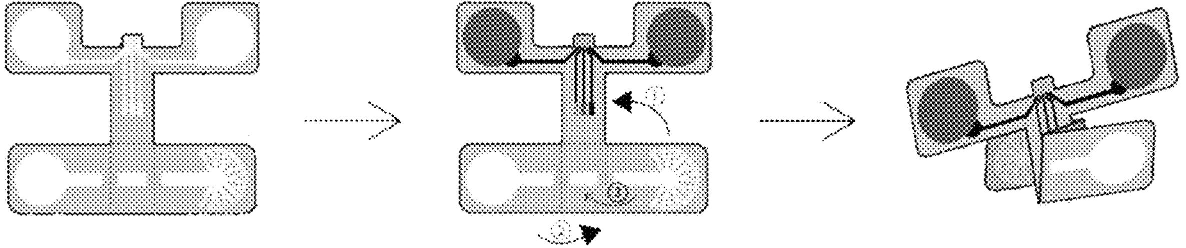
FIG. 3 is a schematic view of a folding process of the paper-based microfluidic patch.
Figure 4:
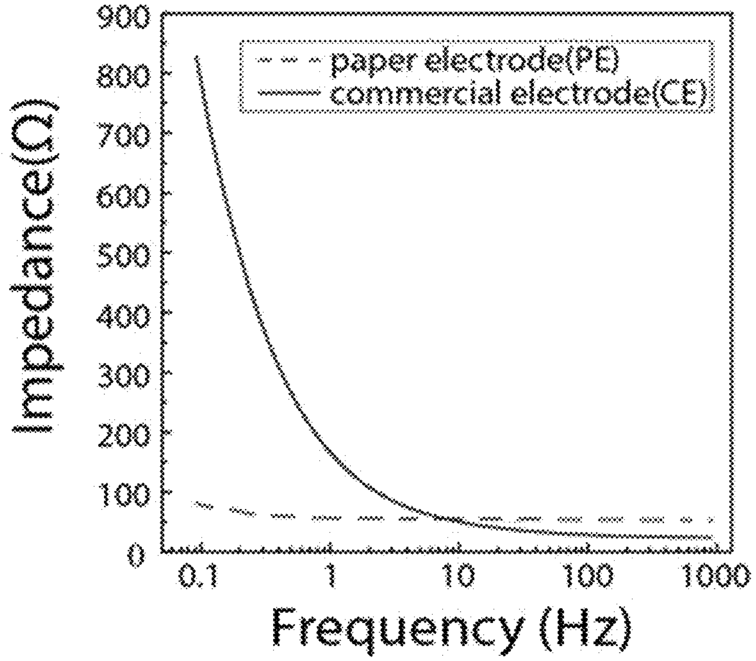
FIG. 4 is a comparison of impedance between an electrocardio electrode in the embodiments of the disclosure and a commercial electrocardio electrode.

In addition, a sweat collection region 401, a reaction region 402, and a sweat evaporation region 403 that are not directly connected to one another are arranged on a plane of the paper-based microfluidic patch 4, and hydrophobic treatment is performed on the rest of the locations. The hydrophobic treatment may be implemented by wax spraying or wax spraying printer treatment. Except for the sweat collection region 401, the reaction region 402, and the sweat evaporation region 403, other regions on the plane of the paper-based microfluidic patch 4 are sprayed with wax, so that sweat cannot penetrate into these regions. However, the three regions of the sweat collection region 401, the reaction region 402, and the sweat evaporation region 403 may achieve the transportation of sweat by utilizing the capillary action of the paper fiber, but the three regions are not connected to one another on the plane and cannot directly transfer moisture. During use, the paper-based microfluidic patch 4 may change the spatial positions of the sweat collection region 401, the reaction region 402, and the sweat evaporation region 403 through 3D folding in space. The folding sequence is shown in FIG. 2: ① first, fold the entire paper-based microfluidic patch 4 toward the electrochemical detection paper-based patch 3, so that the reaction region 402 is in contact with the three-electrode system on the electrochemical detection electrode-paper-based patch 3, ② then fold the sweat evaporation region 403 toward the reaction region 402, so that the sweat evaporation region 403 is in contact with the reaction region 402, and ③ then fold the sweat collection region 401 toward the reaction region 402, so that the sweat collection region 401 and the reaction region 402 are in contact. But it should be noted that the folding directions in steps ② and ③ are different. That is, the sweat evaporation region 403 and the sweat collection region 401 are located on both sides of the reaction region 402, and the electrochemical detection paper-based patch 3 is also attached to one side of the reaction region 402. Therefore, the sweat collection region 401 and the reaction region 402 are actually in indirect contact, with the electrochemical detection paper-based patch 3 between them. However, since the position of the three-electrode system of the electrochemical detection paper-based patch 3 is water-permeable, sweat may still be transferred between the sweat collection region 401 and the reaction region 402. Finally, as shown in FIG. 3, sweat collected in the sweat collection region 401 in a folded state is able to penetrate into the reaction region 402 through a capillary action of the paper-based base layer 1, contact the three-electrode system to generate an oxidation-reduction potential, and then penetrate into the sweat evaporation region 403 to be evaporated. The purpose of designing the paper-based microfluidic patch 4 in a folded form is to allow sweat to come into contact with the three-electrode system while also protecting the electrodes from external interference.

In the disclosure, each of the connection ports 202, the electrode connection lines 304, and the conductive printing port is printed by printing and adopts a two-layer structure, with a lower layer being an Ag/AgCl layer printed on the paper base, and an upper layer being a carbon paste layer to prevent oxidation of the Ag/AgCl layer.

In addition, the flexible detection circuit module 5 certainly includes an electrocardio detection module, an electrochemical detection module, and a wireless communication module, where the electrocardio detection module is used to receive electrical signals from the two electrocardio electrodes 201 for electrocardio detection, the electrochemical detection module is used to receive an electrical signal from the three-electrode system to perform electrochemical detection on the target substance in sweat, and the wireless communication module is used to send a detection result to an external receiving end. Specific circuit structures and forms of the electrocardio detection module, the electrochemical detection module, and the wireless communication module are not limited, as long as the modules can achieve the corresponding functions. The wireless communication module preferably uses Bluetooth for unlimited transmission.

The external receiving end that accepts the detection result may be any terminal, such as a mobile device, a cloud platform, a server, etc. Considering the real-time nature of the result display, it is recommended to use a mobile device with real-time display capabilities, such as a mobile phone, a pad, etc., and a dedicated APP or other software may be installed on the mobile device to display and query the results.

In addition, in order to ensure the accuracy of detection, hydrophobic treatment shall be performed on all regions on the entire paper-based base layer 1, except for the electrocardio electrodes 201, the connection ports 202, the working electrode 301, the electrode connection lines 304, the sweat collection region 401, the reaction region 402, and the sweat evaporation region 403. The hydrophobic treatment may be achieved by spraying wax, or other hydrophobic treatment methods may also be used.

When the device is in use, the device may be attached to the skin of a subject through combination with auxiliary components such as a silicone shell and a PU film, and the electrocardio electrodes 201 and sweat collection region 401 shall be in close contact with the skin. When the subject is exercising, the electrocardio electrodes 201 collect the electrocardio data of the subject in real time. Further, the subject sweats a lot when exercising, and the sweat penetrates into the reaction region 402 through the sweat collection region 401, reacts electrochemically with the electrochemically-sensitive material on the working electrode 301 in the reaction region 402, and thus collects an electrochemical signal in real time through the three-electrode system. The sweat flows through the reaction region 402 and then evaporates through the evaporation region 403. The data collected by the electrocardio electrodes 201 and the three-electrode system are recorded and transmitted by the flexible detection circuit module 5 to the mobile APP for real-time display.

Figure 5:
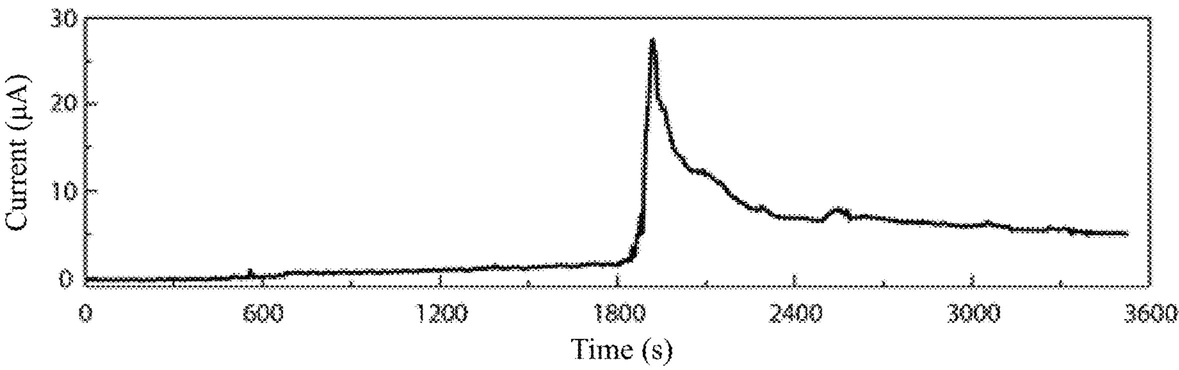
FIG. 5 is body motion test data of the conductive hydrogel paper-based device in this embodiment.
Figure 5:
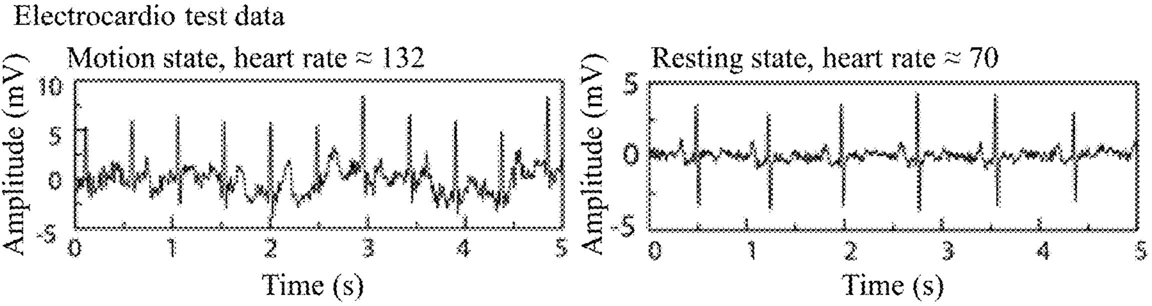

Finally, FIG. 5 demonstrates a set of body motion test data of the conductive hydrogel paper-based device in this embodiment, indicating that this device can achieve non-invasive real-time monitoring of the physiological and biochemical parameters. Further, in order to demonstrate the performance of the conductive paper-based hydrogel electrode in the disclosure, relevant tests are conducted on the electrocardio electrodes 201 and the three-electrode system.

For the test of the electrocardio signal, the electrocardio electrodes 201 in the form of conductive paper-based hydrogel in this embodiment exhibit lower and more stable impedance. This is because the conductive paper-based hydrogel material reduces the electrocardio signal conduction interface and therefore has very good electrical conductivity.

Regarding the electrochemical detection performance of glucose in sweat acting as the detection object, comparing the three-electrode system in this embodiment with other sweat glucose tests in the related art, the conductive paper-based hydrogel electrode in the three-electrode system in this embodiment shows higher sensitivity. The test condition is electrochemical testing, using a 0.6V constant voltage method on an electrochemical workstation, and the liquid environment is PBS or artificial sweat.

| Sensor | Detection range | LOD | Sensitivity | Reference |
|---|---|---|---|---|
| Au/PB/GOx/Ch fiber | 0-500 μM | 6 μM | 11.7 μA $mM^{-1}$ $cm^{-2}$ | (1) |
| Au/rGO/AuPtNP/GOx/nafion | 0-2.4 mM | 5 μM | 48 μA $mM^{-1}$ $cm^{-2}$ | (2) |
| GOx/CNTs/Ti3C2Tx/ PB/CFMs | 10 μM-1.5 mM | 0.33 μM | 35.3 μA $mM^{-1}$ $cm^{-2}$ | (3) |
| CoWO4/CNT | 0-0.3 mM | 1.3 μM | 10.89 μA $mM^{-1}$ $cm^{-2}$ | (4) |
| WSNF | 1 μM-1 mM | 500 nM | 140 μA $mM^{-1}$ $cm^{-2}$ | (5) |
| GOx/chitosan/CNT/ PB | 0-200 μM | — | 8 μA $mM^{-1}$ | (6) |
| GOx/chitosan/Pt/SilkNCT | 25-300 μM | 5 μM | 6.3nA $\mu M^{-1}$ | (7) |
| Au/MWCNT/PtNP/PPD/GOx | 0-300 μM | — | 59 ± 12 μA $mM^{-1}$ $cm^{-2}$ | (8) |
| GOx/A1203 nanoparticles/ NiHCF/PB/Au | 0-200 μM | 10 μM | 41.8 nA $\mu M^{-1}$ $cm^{-2}$ | (9) |
| Au-Si-MNA/ Fc-PAMAM/GOx | 1-11 mM | 0.45 nM | 0.58 μA $mM^{-1}$ $cm^{-2}$ | (10) |
| The disclosure | 0-12 Mm | 10.3 μM | 325.99 ± 0.8 μA $mM^{-1}$ $cm^{-2}$ | Our work |

The references for the above related art are as follows:

1. Y. M. Zhao, Q. F. Zhai, D. S. Dong, T. C. An, S. Gong, Q. Q. Shi, W. L. Cheng, A Highly Stretchable and Strain-Insensitive Fiber-Based Wearable Electrochemical Biosensor to Monitor Glucose in the Sweat. Analytical chemistry 91, 6569-6576 (2019).

2. X. Xuan, H. S. Yoon, J. Y. Park, A wearable electrochemical glucose sensor based on simple and low-cost fabrication supported micro-patterned reduced graphene oxide nanocomposite electrode on flexible substrate. Biosensors & bioelectronics 109, 75-82 (2018).
3. Y. J. Lei, E. N. Zhao, Y. Z. Zhang, Q. Jiang, J. H. He, A. Baeumner, O. S. Wolfbeis, Z. L. Wang, K. N. Salama, H. N. Aishareef, A MXene-Based Wearable Biosensor System for High-Performance In Vitro Perspiration Analysis. Small (Weinheim an der Bergstrasse, Germany) 15, (2019).
4. S. Y. Oh, S. Y. Hong, Y. R. Jeong, J. Yun, H. Park, S. W. Jin, G. Lee, J. H. Oh, H. Lee, S. S. Lee, J. S. Ha, Skin-Attachable, A Skin-Attachable, Stretchable Electrochemical Sweat Sensor for Glucose and pH Detection. ACS applied materials & interfaces 10, 13729-13740 (2018).
5. P. T. Toi, T. Q. Trung, T. M. L. Dang, C. W. Bae, N. E. Lee, Highly Electrocatalytic, Durable, and Stretchable Nanohybrid Fiber for On-Body Sweat Glucose Detection. ACS applied materials & interfaces 11, 10707-10717 (2019).
6. X. C. He, S. J. Yang, Q. B. Pei, Y. C. Song, C. H. Liu, T. L. Xu, X. J. Zhang, Integrated Smart Janus Textile Bands for Self-Pumping Sweat Sampling and Analysis. ACS sensors 5, 1548-1554 (2020).
7. W. Y. He, C. Y. Wang, H. M. Wang, M. Q. Jian, W. D. Lu, X. P. Liang, X. Zhang, F. C. Yang, Y. Y. Zhang, Integrated textile sensor patch for real-time and multiplex sweat analysis. Science Advances 5, (2019).
8. X. B. Cheng, B. Wang, Y. C. Zhao, H. Hojaiji, S. Y. Lin, R. Shih, H. S. Lin, S. Tamayosa, B. Ham, P. Stout, K. Salahi, Z. Q. Wang, C. Z. Zhao, J. W. Tan, S. Emaminejad, A Mediator-Free Electroenzymatic Sensing Methodology to Mitigate Ionic and Electroactive Interferents' Effects for Reliable Wearable Metabolite and Nutrient Monitoring. Advanced Functional Materials 30, (2020).
9. Y. J. Lin, M. Bariya, H. Y. Y. Nyein, L. Kivimaki, S. Uusitalo, E. Jonsson, W. B. Ji, Z. Yuan, T. Happonen, C. Liedert, J. Hiltunen, Z. Y. Fan, A. Javey, Porous Enzymatic Membrane for Nanotextured Glucose Sweat Sensors with High Stability toward Reliable Noninvasive Health Monitoring. Advanced Functional Materials 29, (2019).
10. M. Dervisevic, M. Alba, L. Yan, M. Senel, T. R. Gengenbach, B. Prieto-Simon, N. H. Voelcker, Transdermal Electrochemical Monitoring of Glucose via High-Density Silicon Microneedle Array Patch. Advanced Functional Materials, (2021).

The above-described embodiments are only preferred solutions of the disclosure, but the embodiments are not intended to limit the disclosure. A person having ordinary skill in the art can also make various changes and modifications without departing from the spirit and scope of the disclosure. Therefore, any technical solutions obtained by equivalent substitution or equivalent transformation fall within the protection scope of the disclosure.

What is claimed is:

1. A conductive hydrogel paper-based device for synchronously monitoring physiological and biochemical parameters, comprising a paper-based module and a flexible detection circuit module;

wherein the paper-based module is divided into three parts, a first part of the three parts is two pieces of electrocardio electrode paper-based patches, a second part of the three parts is one piece of an electrochemical detection paper-based patch, a third part of the three parts is one piece of a paper-based microfluidic patch, and the three parts are integrated and processed on a same paper-based base layer, wherein each of the two pieces of the electrocardio electrode paper-based patches forms an electrocardio electrode by being added with a conductive hydrogel material through dripping on the paper-based base layer, wherein the electrochemical detection paper-based patch forms a working electrode by being added with the conductive hydrogel material through dripping on the paper-based base layer, and the working electrode is decorated with an electrochemically-sensitive layer, wherein a reference electrode and a counter electrode are both attached to the paper-based base layer to form a three-electrode system, and the conductive hydrogel material is made of a mixture of conductive polymer PEDOT:PSS and ionic liquid, wherein the electrocardio electrodes, the working electrode, the reference electrode, and the counter electrode are individually connected to a conductive printing port of the flexible detection circuit module through electrode connection lines, wherein electrical signals of the electrocardio electrodes, an electrical signal of the working electrode, an electrical signal of the reference electrode, and an electrical signal of the counter electrode are sent to the flexible detection circuit module for processing and external transmission, wherein a sweat collection region, a reaction region, and a sweat evaporation region are not directly connected to one another, and the sweat collection region, the reaction region, and the sweat evaporation region are arranged on a plane of the paper-based microfluidic patch, wherein hydrophobic treatment is performed on the rest of the plane of the paper-based microfluidic patch, and the paper-based microfluidic patch is able to make the reaction region in contact with the three-electrode system on the electrocardio electrode paper-based patches through 3D folding, wherein the sweat evaporation region and the sweat collection region individually contact the reaction region, and sweat collected in the sweat collection region in a folded state is able to penetrate into the reaction region through a capillary action of the paper-based base layer, contact the three-electrode system to generate an oxidation-reduction potential, and then penetrate into the sweat evaporation region to be evaporated.

2. The conductive hydrogel paper-based device for synchronously monitoring the physiological and biochemical parameters according to claim 1, wherein the reference electrode and the counter electrode are printed on the paper-based base layer through a screen printing process.

3. The conductive hydrogel paper-based device for synchronously monitoring the physiological and biochemical parameters according to claim 1, wherein the ionic liquid is dodecylbenzenesulfonic acid or 1-ethyl-3-methylimidazole.

4. The conductive hydrogel paper-based device for synchronously monitoring the physiological and biochemical parameters according to claim 1, wherein the electrochemically-sensitive layer is a biochemical reagent or a catalytic material.

5. The conductive hydrogel paper-based device for synchronously monitoring the physiological and biochemical parameters according to claim 4, wherein the catalytic material is at least one of Pt nanoparticles and Au nanoparticles.

6. The conductive hydrogel paper-based device for synchronously monitoring the physiological and biochemical parameters according to claim 1, wherein the electrochemically-sensitive layer is a biochemical reagent, and the biochemical reagent is one or more of glucose oxidase, glucose dehydrogenase, lactate oxidase, urate oxidase, cholesterol oxidase, phospholipase, amino acid enzyme, horseradish peroxidase, β-hydroxybutyrate dehydrogenase, Prussian blue, and ferrocene methanol.

7. The conductive hydrogel paper-based device for synchronously monitoring the physiological and biochemical parameters according to claim 1, wherein the electrocardio electrodes are two circular paper-based electrodes, and circular edges are provided with connection ports for connection to the electrode connection lines.

8. The conductive hydrogel paper-based device for synchronously monitoring the physiological and biochemical parameters according to claim 7, wherein each of the connection ports, the electrode connection lines, and the conductive printing port is printed by printing, with a lower layer being an Ag/AgCl layer and an upper layer being a carbon paste layer.

9. The conductive hydrogel paper-based device for synchronously monitoring the physiological and biochemical parameters according to claim 7, wherein the flexible detection circuit module comprises an electrocardio detection module, an electrochemical detection module, and a wireless communication module, wherein the electrocardio detection module is used to receive electrical signals from the two electrocardio electrodes for electrocardio detection, and the electrochemical detection module is used to receive an electrical signal from the three-electrode system to perform electrochemical detection on a target substance in sweat, and the wireless communication module is used to send a detection result to an external receiving end.

10. The conductive hydrogel paper-based device for synchronously monitoring the physiological and biochemical parameters according to claim 9, wherein the external receiving end is a mobile device with a real-time display function.

* * * * *